US005938919A

United States Patent [19]
Najafabadi

[11] Patent Number: 5,938,919
[45] Date of Patent: Aug. 17, 1999

[54] FUSED SILICA CAPILLARY COLUMNS PROTECTED BY FLEXIBLE SHIELDING

[75] Inventor: Bijan Modrek Najafabadi, San Pedro, Calif.

[73] Assignee: Phenomenex, Torrance, Calif.

[21] Appl. No.: 08/859,349

[22] Filed: May 20, 1997

Related U.S. Application Data

[63] Continuation of application No. 08/577,270, Dec. 22, 1995, abandoned.

[51] Int. Cl.$^6$ .................................................. B01D 15/08
[52] U.S. Cl. ........................... 210/198.2; 210/656; 96/101
[58] Field of Search ................. 210/656, 198.2; 95/82; 96/101

[56] References Cited

U.S. PATENT DOCUMENTS

| | | | |
|---|---|---|---|
| 3,570,673 | 3/1971 | Dutz | 210/198.2 |
| 3,856,669 | 12/1974 | Ito | 210/198.2 |
| 4,293,415 | 10/1981 | Bente | 210/198.2 |
| 4,375,163 | 3/1983 | Yang | 210/198.2 |
| 4,424,127 | 1/1984 | Roeraade | 210/198.2 |
| 4,483,773 | 11/1984 | Yang | 210/198.2 |
| 4,726,822 | 2/1988 | Cates | 210/198.2 |
| 4,729,823 | 3/1988 | Guevara, Jr. | 204/299 R |
| 5,057,216 | 10/1991 | Chervet | 210/198.2 |
| 5,082,559 | 1/1992 | Eguchi | 210/198.2 |
| 5,141,548 | 8/1992 | Chervet | 65/108 |
| 5,194,225 | 3/1993 | Muller | 210/198.2 |
| 5,205,154 | 4/1993 | Lee | 73/23.35 |
| 5,326,412 | 7/1994 | Schreiber | 156/150 |
| 5,340,475 | 8/1994 | Cortes et al. | 210/198.2 |
| 5,423,513 | 6/1995 | Chervet et al. | 250/227.25 |
| 5,552,042 | 9/1996 | Le Febre | 210/198.2 |

OTHER PUBLICATIONS

Hawley's Condensed Chemical Dictionary, Eighth Edition, 1971, Van Nostrand Reinhold Company, p. 350.
Snyder, Introduction to Modern Liquid Chromatography, John Wiley & Sons, 1979, pp. 203–204.
Price List/Ordering Information (Jun. 1994); LC Packings, Switzerland, pp. 1–7.
Micro—Everything for Micro, Capillary and Nano LC: Packed Columns, Microflow Processors, UV Flow Cells, LC/MS Interface, Accessories (1994); LC Packings, Switzerland pp. 1–12.
Micro–Tech Scientific, Innovations in Microcolumn Separations; Microtech Scientific pp. 1–29.
Excerpts from Upchurch Scientific Catalog (I), pp. 1–29.
Excerpts from Upchurch Scientific Catalog (II), pp. 18–23 and 46–47 & 30–31.

*Primary Examiner*—Ernest G. Therkorn
*Attorney, Agent, or Firm*—Knobbe, Martens, Olson & Bear, LLP

[57] ABSTRACT

A protected fused-silica capillary liquid chromatography (liquid chromatography) column is shielded inside a single flexible tubing, which has the same length as the capillary and is integrated with the capillary in the packing process. The column has the advantages of a fused-silica capillary liquid chromatography column combined with the benefits of the shield tubing which makes the column more accurate, durable, and convenient to use, and less expensive to produce.

28 Claims, 5 Drawing Sheets

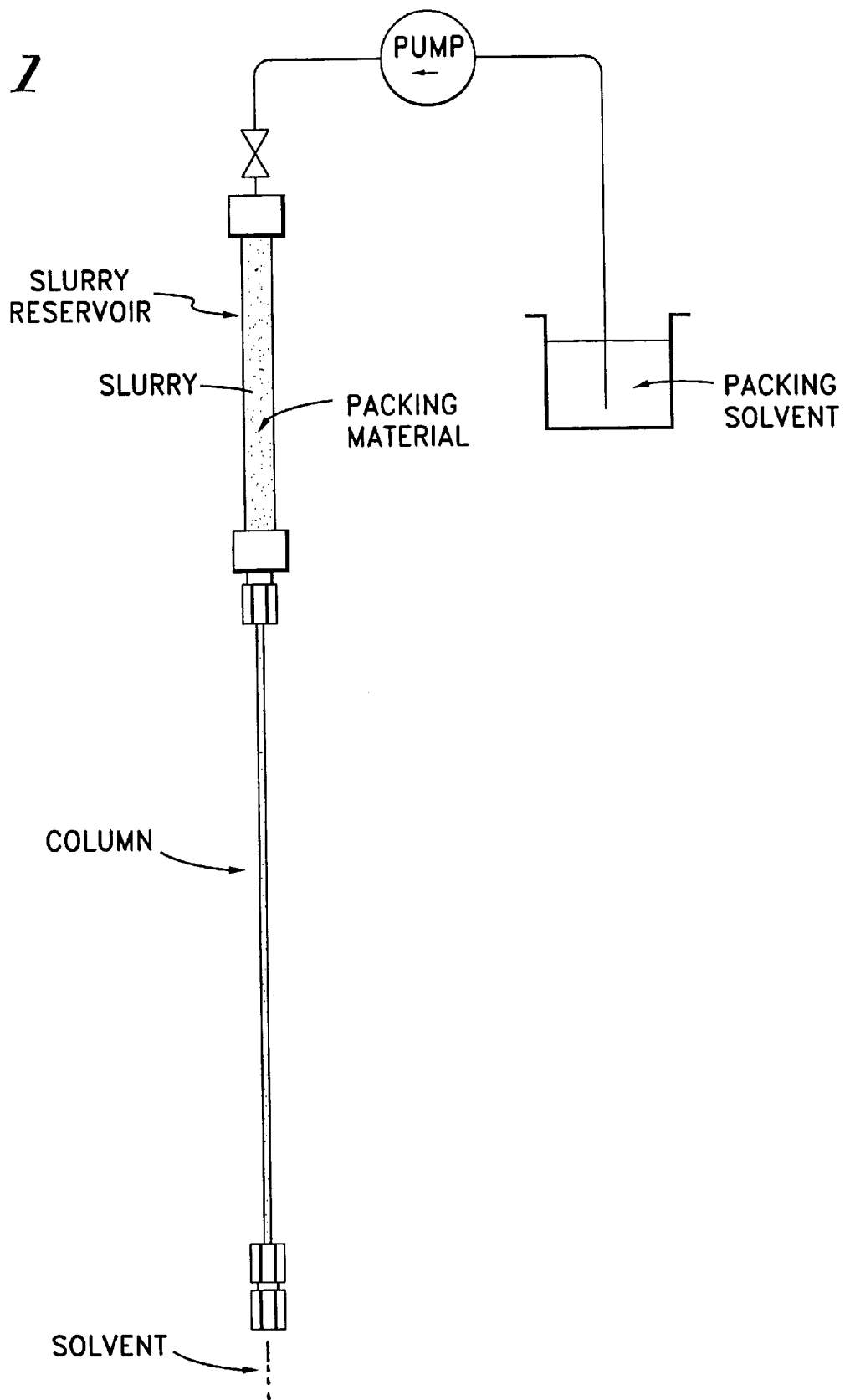

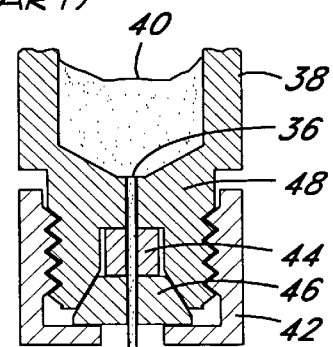
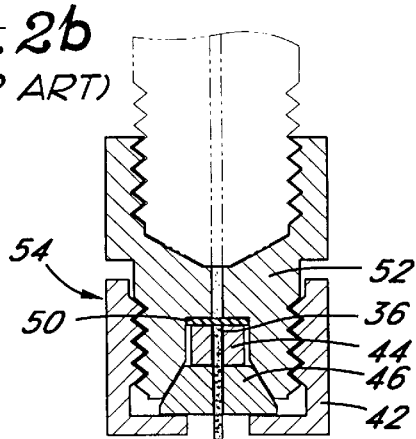
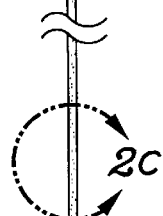
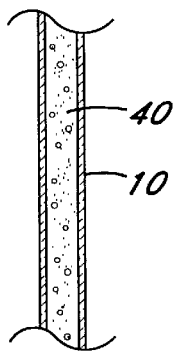
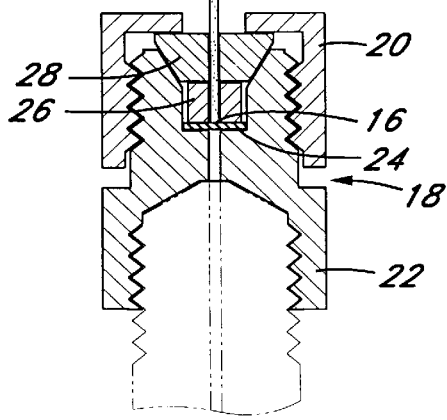
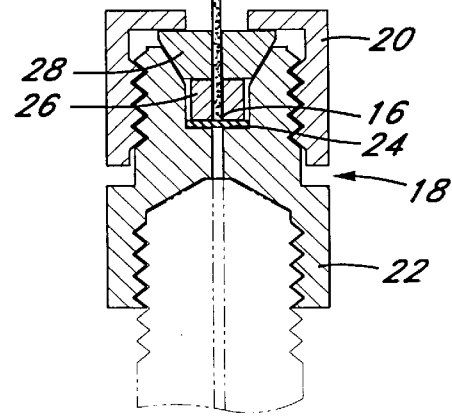

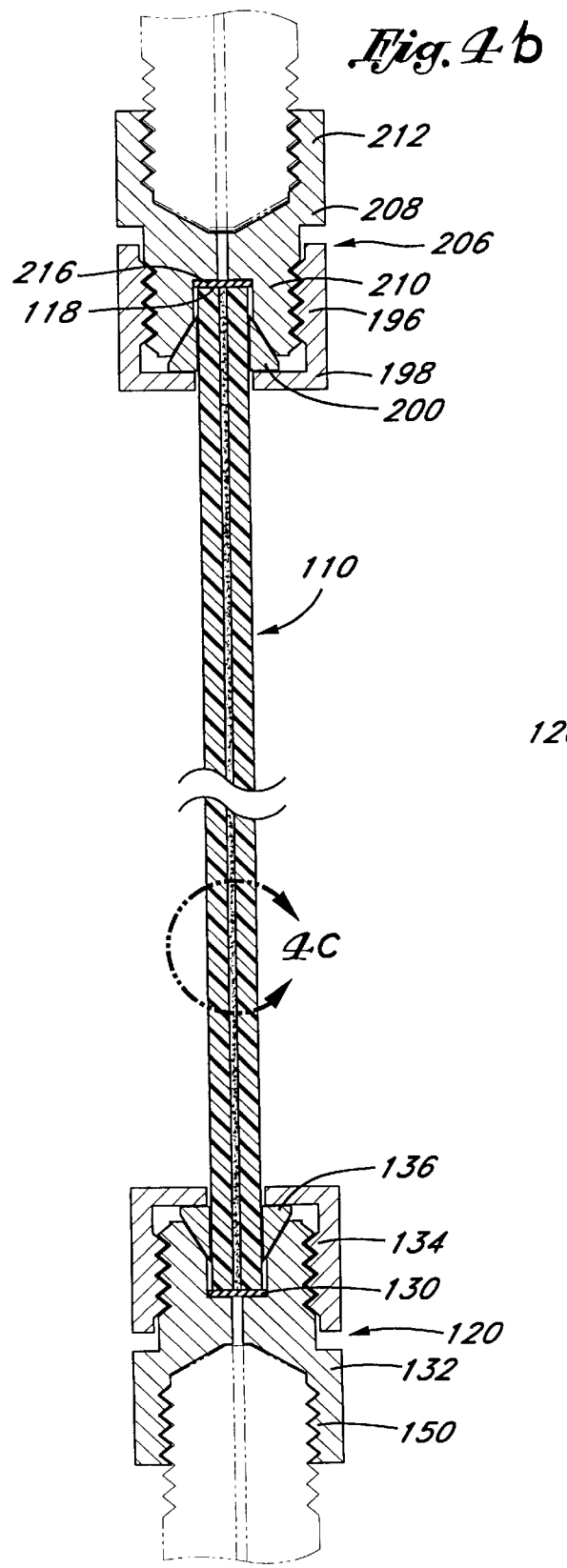

FUSED SILICA CAPILLARY COLUMNS PROTECTED BY FLEXIBLE SHIELDING

This application is a continuation of U.S. patent application Ser. No. 08/577,270, filed Dec. 22, 1995, now abandoned.

FIELD OF THE INVENTION

This invention relates to a capillary liquid chromatography (capillary LC) column, and more particularly to a shielded fused silica capillary LC column with an inner diameter of about 0.7 mm or less.

BACKGROUND OF THE INVENTION

In a liquid chromatographic system, the LC column is located between an injector and an LC detector to separate one or more constituents of interest from the various interferences in a sample to permit detection of these constituents of interest by an LC detector.

Capillary LC is a micro-version of traditional liquid chromatography and its popularity has grown rapidly during the past decade. Capillary LC columns have extremely low solvent consumption and require ultra-low volumes of samples for analysis, and hence provide high efficiency separations. Analogous to traditional liquid chromatography, capillary LC consists of a micro-pump, a capillary column, a detector, and a data processing device. The capillary column is important to the system because it is where the separation process occurs.

A capillary LC column is manufactured by packing a capillary column with separation media, such as bonded silica particles, also referred to as packing material. As schematically illustrated in FIG. 1, a slurry is used in a packing process. The slurry includes a packing material mixed with a slurry solvent, and is housed in a reservoir adjacent the column. To pack the column, a packing solvent is pumped to the slurry reservoir to drive the slurry into the column, which allows the solvent to pass through but not the packing material, thereby packing the column with the separation media.

Different types of materials, such as fused silica, stainless steel, and polymer, have been used for the capillary column. Due to their unique features, fused silica capillaries are the most common for preparation of capillary LC columns. Fused silica capillary columns have inner diameters of less than 1 mm and, typically, less than 0.7 mm. They are strong and can withstand high packing pressure, e.g., at least 9000 psi. It is easy to control their column dimensions during manufacturing, and the columns do not deform during packing. Further, the wall of a fused silica capillary is smooth, which is very desirable for packing.

Although fused silica capillaries have some unsurpassed advantages, they do have certain limitations. The most significant limitation stems from the brittle and fragile nature of the glass-like material from which they are made. The frangible nature of a thin, fused silica tube makes packing, shipping, and handling difficult. A layer of polyimide is generally coated on the outside of the fused silica capillary for protection. However, if the polyimide layer has incurred even a small scratch during production or handling, it will lose its effect and the capillary can break with just a gentle touch.

To avoid damage to the packed capillary LC column, a shielding of stainless steel is sometimes provided for protection. Although the currently available steel shieldings do prevent the capillaries from breaking, they are rigid and thus require long connecting tubings to install the capillary column between the injector and the detector of an LC system. This generates unnecessary extra column dead volume which degrades separation efficiency. Moreover, a separate assembling process is required in addition to the packing process, which can add extra cost to capillary LC column production.

Another problem with fused silica capillary columns is the difficulty of achieving an exact length for the packed column. Errors of 1–2 mm in length are common.

In addition, a sleeve is needed to tighten and secure an end-fitting on the end of the capillary column. During the packing process, one end of the capillary is typically enclosed with an end-fitting assembly and the other end is connected to a slurry reservoir. A flexible sleeve is employed in the end-fitting assembly during packing because sufficient tightening is required to enclose the end for high pressure packing. The sleeve facilitates tightening and compensates for the size of the capillary, which is too narrow for the end-fitting. The packing pressure can force the end-fitting assembly open if there is insufficient tightening, while too much tightening can damage the capillary.

There is a need, therefore, for a device that can protect the capillary during packing and handling, and alleviate the other shortcomings of the fragile fused silica capillary.

SUMMARY OF THE INVENTION

The present invention uses a flexible tubing as a shielding for a capillary column to form a shielded capillary LC column. The flexible tubing is assembled onto the fused silica capillary before packing the column with packing material to protect the capillary during the packing process, and is integrated into the finished product. The flexible tubing is preferably made of a polymer and shields the entire fused silica portion of the capillary column. It thus has the same or substantially the same length as the silica capillary column in the finished product. The ends of the housed capillary column are secured into standard LC end-fittings and are sealed by conventional ferrules, but no sleeves are needed as in the prior art.

There is thus advantageously provided a liquid chromatography column with a silica based capillary having a wall structure defining an elongated internal cavity with first and second ends. A flexible, protective tubular shield encloses the exterior of the wall structure for substantially the entire length of the column. Preferably, the capillary is made of fused silica, with the shield slip-fit over the capillary. Advantageously, the shield is made of PEEK. The shield may be bonded to the capillary with an epoxy.

The liquid chromatography column may be packed with a packing material retained by a first frit disposed at an opening at a first end of the liquid chromatography column and a second frit disposed at an opening at a second, opposing end of the liquid chromatography column. The first and second frits prevent the packing material from passing through but allow the liquid solvent to pass. Preferably, the frit comprises a stainless steel material.

The present invention also comprises a method of assembling and packing a liquid chromatography column by providing a slurry which includes a packing material and a packing solvent. A silica based capillary column having a first open end and a second open end is also provided. A flexible shielding is slip-fit onto said capillary column. The first open end is covered with a first frit that allows said packing solvent but not said packing material to pass therethrough. Finally, the slurry is injected into the capillary column through the second open end. Advantageously, the capillary is made of fused silica, and the flexible shielding is a PEEK cylindrical tubing having an inner diameter slightly larger than the outer diameter of the capillary and a length slightly smaller than the length of said capillary such that the extra length of said capillary protrudes from said flexible tubing at the second open end of the liquid chromatography column.

Because the shielded capillaries are not only flexible, but more resistant to breakage than prior art capillary columns made of glass or of fused silica, the present invention also comprises a capillary product made by the methods described above, and as more fully described hereinafter.

It is an object of the present invention to provide a shielding to protect the fused silica capillary LC column from damage during packing of the column with media, and shipping and handling.

Another object of the invention is to provide a shielded capillary LC column that is flexible and can be directly connected to an injector at one end and to a detector at the other end in order to minimize extra column dead volume, thereby improving separation efficiency.

An additional object of the invention is to provide an exact and repeatable column length for the LC column.

Another object is to more easily achieve a sufficient screw tightening pressure to hold the end-fittings onto the capillary column during high pressure packing without damaging the LC column.

Yet another object of the invention is to provide a method to integrate the assembling process into the packing process to decrease production cost.

BRIEF DESCRIPTION OF THE DRAWINGS

FIG. 1 is a front elevational view illustrating an LC column assembled for packing;

FIG. 2a is a cross-sectional view of an existing capillary column set up for packing;

FIG. 2b is a cross-sectional view of an assembled and packed capillary LC column of FIG. 2a;

FIG. 2c is a close-up cross-sectional view of the capillary LC column of FIG. 2a;

FIG. 4b is a cross-sectional view of an assembled and packed capillary column of FIG. 4a;

FIG. 4c is a close-up cross-sectional view of the packed capillary LC column of FIG. 4b.

DESCRIPTION OF THE INVENTION

Figure 3:
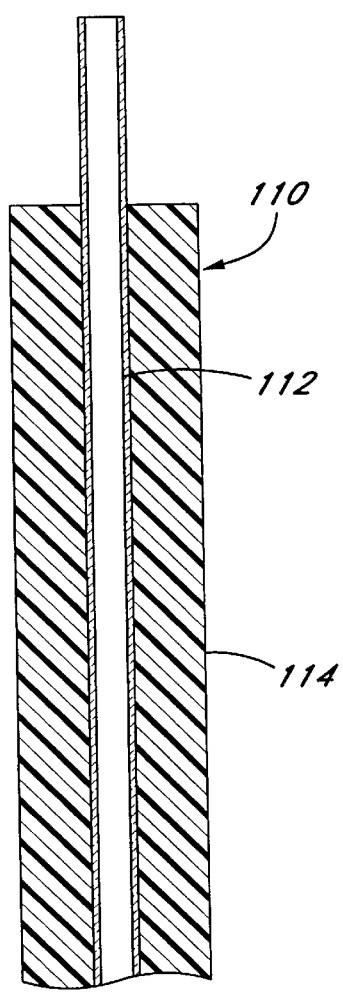
FIG. 3 is a cross-sectional view of a preferred embodiment of a shielded capillary column of the present invention.

Prior Art Packing Process Referring to FIGS. 1 and 2a, to pack the capillary column 10, a first end 16 of the capillary 10 is enclosed with an end-fitting assembly 18, which comprises a swaging nut 20, an end nut 22, a frit 24, a sleeve 26, and a ferrule 28. The frit 24 allows packing solvent to pass through while keeping the packing material 32 in the capillary LC column 10 (FIG. 2c). The ferrule 28 and the sleeve 26 serve to secure and seal the capillary 10 to the end-fitting assembly 18 as the swaging nut 20 and end nut 22 are threaded and tightened together. The sleeve 26 is made of a flexible, deformable material to protect the brittle and fragile fused silica capillary 10, and to fill the space between the swaging nut 20 and end nut 22 and seal it under pressure. The deformable sleeve 26 sustains relatively high screw tightening pressure for the end-fitting assembly 18 without damage to the fused silica capillary 10.

The opposing second end 36 of the fused silica capillary 10 is then connected to a slurry reservoir 38 of slurry 40 which includes the packing material 32 mixed in a solvent. Pressure is applied to fill and pack the capillary 10 with the packing material 32. The solvent passes through the column 10 from the end 36 to the end 16, and out through the frit 24, as illustrated in FIGS. 2a and 2c.

Since the packing process usually requires high pressure, the capillary 10 has to be secured tightly to the slurry reservoir 38. This is accomplished by tightening a threaded swaging nut 42 onto threaded mounting portion 48 on slurry reservoir 38. The nut 42 presses and grips a sleeve 44 and conical ferrule 46 against the capillary 10. Too much tightening will damage the fused silica capillary 10 due to its fragile nature. On the other hand, if the capillary 10 is not sufficiently tightened, it will be pushed away from, and even off the mounting portion 48, and thus separate from the reservoir 38 by the high pressure applied during packing. The sleeves 26, 44 are commonly made of PTFE (Polytetrafluoroethylene), and the ferrule 46 is made of graphite.

FIG. 2b shows the packed column 12 after packing is finished and pressure is gradually removed, and the mounting portion 48 of the reservoir 38 (FIG. 2a) is replaced by a frit 50 and an end nut 52. The end nut 52 is screwed onto the swaging nut 42 and, together with the cylindrical sleeve 44, conical ferrule 46, and frit 50, form the second end-fitting assembly 54 to enclose the end 36 of the packed column 12. The packed column 12 hence contains packing material 32 enclosed by two end-fitting assemblies 18 and 54 that are substantially identical in construction.

Detailed Description of the Preferred Embodiments

A preferred embodiment of a shielded capillary column 110 of the present invention is illustrated in FIG. 3. The column 110 comprises a capillary column 112, advantageously made of a silica based material, such as glass, and preferably made of fused silica which is more flexible than glass capillaries. The column 112 is housed in a shield tubing 114, that advantageously extends for substantially the full length of the capillary column 112 as shown in the figures. The capillary 112 advantageously has an inner diameter of less than 1 mm, and preferably less than 0.7 mm. The tubing 14 is desirably flexible and made of polymer, and preferably made of PEEK (Polyetheretherketone). The tubing 114 serves as a shield to prevent even accidental scratching of the polyimide layer that would cause the capillary 112 to fracture. The shield tubing 114 is desirably slip-fitted onto the capillary 112, with the inner wall of the tubing 114 forming a cavity slightly larger than the capillary 112 and being spaced close to the external surface of the capillary 112. The space between the exterior surface of capillary 112 and the interior surface of tubing 114 is preferably as small as possible, while still allowing the tube 114 to be slip-fitted over the capillary column 112. Note that the capillary 112 is longer than the shield tubing 114 so that it can be cut to match the exact length of the shield tubing 114 in the assembled and finished product.

Figure 4A:
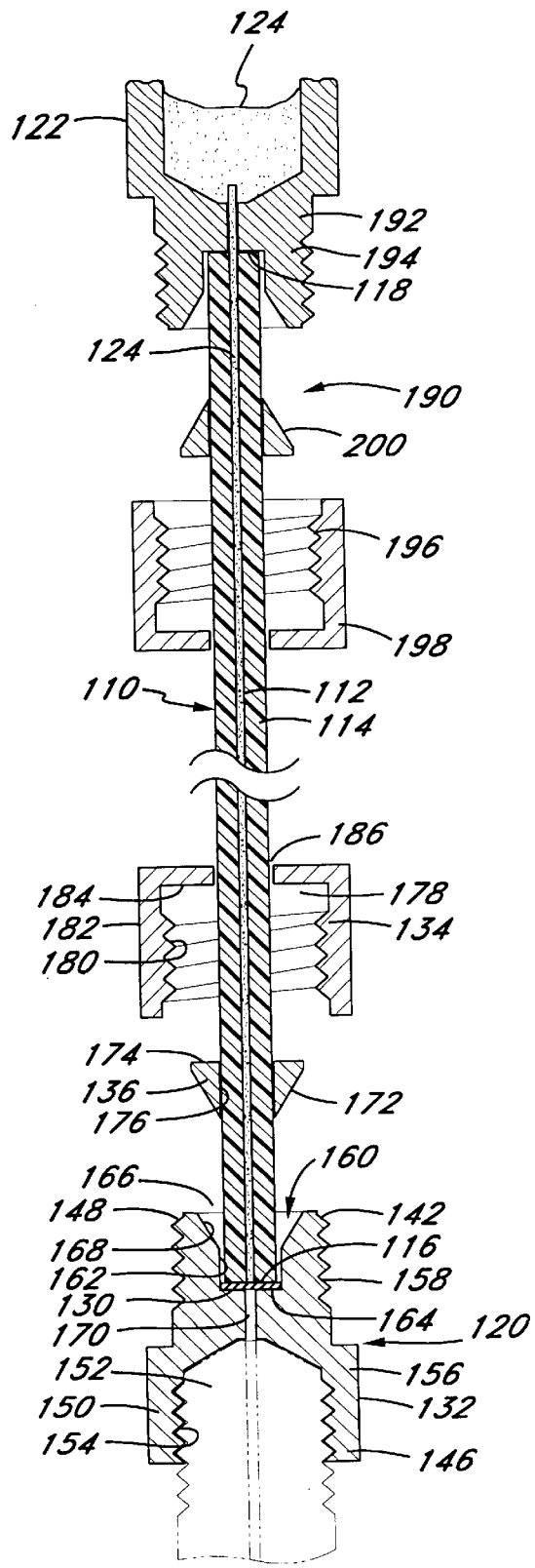
FIG. 4a is an exploded schematic cross-sectional view of the capillary column of FIG. 3 set up for packing.

FIG. 4a illustrates the capillary LC column 110 set up for packing. The column 110 is advantageously a hollow, cylindrical tube having a first end 116 and a second end 118 substantially perpendicular to the axial length of the column 110. The first end 116 is enclosed by a first end-fitting 120 shown in the exploded view in FIG. 4a. The second end 118 is connected to a slurry reservoir 122 of slurry 124, which includes packing material 126 mixed in a solvent.

The first end-fitting assembly 120 includes a frit 130 that is placed at the opening of the column 110 at the first end 116. The frit 130 is a circular-disc screen which permits the packing solvent, but not the packing material 126, to pass through during the packing process. The frit 130 is held in place by an end nut 132 threaded into a swaging nut 134, and secured and sealed by conical ferrule 136 disposed between the end nut 132 and swaging nut 134. The frit 130, end nut 132, swaging nut 134, and ferrule 136 are all preferably symmetrical about the longitudinal axis of the column 110.

The end nut 132 has a first end 142 and a second end 146. The first end 142 has a male screw portion 148 and the second end 146 has a female screw portion 150. The female screw portion 150 has a wall structure which defines a cavity 152 with internal threads 154, and desirably has a circular cylindrical external surface 156. The male screw portion 148 includes a wall structure which has external threads 158 and defines a cavity 160 desirably having a circular cylindrical inner wall 162 and a flat circular seat 164.

The diameter of the inner wall 162 is desirably slightly greater than the outer diameter of the shield capillary column 110 for proper fit between the cavity 160 and column 110. The cavity 160 opens toward the column 110, through opening 166. The opening 166 of the cavity 160 at the first end 142 advantageously has a taper 168 which forms a truncated conical cavity portion with a larger diameter at the opening 166 than at the inner wall 162. A flow passage 170 disposed along the axis of the end nut 132 connects the cavity 152 and cavity 160. The passage 170 desirably is of cylindrical shape with an inner diameter approximately 200 μm.

The frit 130 is disposed between the first end 116 of the capillary column 110 and the seat 164 of the cavity 160 of the end nut 132. The frit 130 desirably is a flat, circular-disc screen with a plurality of small holes which are sized to permit the solvent but not packing material 126 to pass through. The frit 130 advantageously has a surface area larger than the cross-sectional area of the capillary column 110, and closely fits on the seat 164.

The ferrule 136 is a truncated conical member with a conical portion 172, flat portion 174, and hollow portion 176 at the center. The conical portion 172 desirably matches the truncated conical cavity portion of the taper 168 at the opening 166 of the end nut 132. The hollow portion 176 preferably has a cylindrical shape with an inner diameter ("ID") slightly larger than the outer diameter ("OD") of the shielded capillary column 110 to provide a slip fit.

The swaging nut 134 is provided to cooperate with the end nut 132 and ferrule 136. The swaging nut 134 desirably has a wall structure which defines a cavity 178 with internal threads 180 and circular cylindrical external surface 182. The internal threads 180 match the external threads 158 of the male screw portion 148 of the end nut 132. The swaging nut 134 desirably has a flat seat 184 in the cavity 178 which seat faces the end nut 132 and cooperates the flat portion 174 of the ferrule 136. At the center of the swaging nut 134 is a circular hole 186 which is sized to slide over the outer surface of the column 110.

The end nut 132 and swaging nut 134 are tightened by turning one relative to the other, as illustrated in the assembled first end-fitting assembly 120 in FIG. 4b. The taper 168 of the end nut 132 cooperates with the conical portion 172 of the ferrule 136 while the seat 184 of the swaging 134 cooperates with the flat portion 174 of the ferrule 136. As the end nut 132 and swaging nut 134 are tightened and drawn together along the longitudinal axis of the column 110, the taper 168 transfers the longitudinal force into a radial force acting toward the radial axis of the ferrule 136 and column 110. Thus, tightening the nut 134 causes the ferrule 136 to squeeze and in turn grip the shield 114 of the column 110, to seal the column 110 with the end-fitting assembly 120. No sleeve is needed, and the screw tightening pressure can be effected more accurately than in the prior art.

The column 110 can be secured to the slurry reservoir 122 in any appropriate way. FIG. 4a shows a locking assembly 190 which operates in much the same way as the first end-fitting assembly 120. The locking assembly 190 includes a mounting portion 192 on the reservoir 122 having a male screw portion 194 which cooperates with a female screw portion 196 of a second swaging nut 198. A second ferrule 200 is disposed between the mounting portion 192 and swaging nut 198. The second ferrule 200 is desirably the same as the first ferrule 136 and the second swaging nut 198 the same as swaging nut 134. The locking assembly 190 is used to threadingly secure the column 110 to the reservoir 122 prior to packing, with a length of the capillary 112 (but not the shield 114) extending through an axially located aperture in mounting portion 192.

Once connected, the shielded column 110 is packed as in the same way as any other column. After packing, the extra length of the capillary 112 at the second end 118 is removed to produce a flushed second end 118, as best seen in FIG. 4b. That is, the free length of capillary 112 that extended beyond shield 114 (FIGS. 3, 4a) is cut flush with the end of the shield 114. This allows much more accurate and repeatable control over the length of the capillary 112 and hence the shielded LC column 110.

FIG. 4c is a close-up view of the packing material 126 packed inside the capillary 112. The second end 118 of the column 110 is then enclosed with a second end-fitting assembly 206. The second end-fitting assembly 206 includes a second end nut 208 with a male screw portion 210 and a female screw portion 212, and holding a second frit 216 at the second end 118 of the column 110. The second end nut 208 is desirably the same as the first end nut 132 and the second frit 216 the same as the first frit 130. The male screw portion 210 of the second end nut 208 engages the female screw portion 196 of the second swaging nut 198 with the ferrule 200 disposed in between to secure and seal the frit 216 to the column 110 in the same way as in the first end-fitting assembly 120. The female screw portion 150 of the first end nut 132 and the female screw portion 212 of the second end nut 208 provide female connecting ports to permit easy connection to an injector or detector, by male-female coupling.

One advantage of this packing method is that the assembling process is integrated into the packing process. The first end-fitting assembly 120 is constructed as the column 110 is prepared for packing. The swaging nut 198 and ferrule 200 are also provided as part of the packing set-up. After packing, the swaging nut 198 is disengaged from the mounting portion 192 of the reservoir 122. The capillary 112 is cut to match the shield 114 in length and then the second frit 216 is placed at the second end 118 and enclosed by the second end nut 208. This integration of assembling and packing makes preparation of the packed LC column 110 fast and efficient and hence decreases production cost. It also results in a more accurate, and repeatable control of the length of the column 110.

Figure 5:
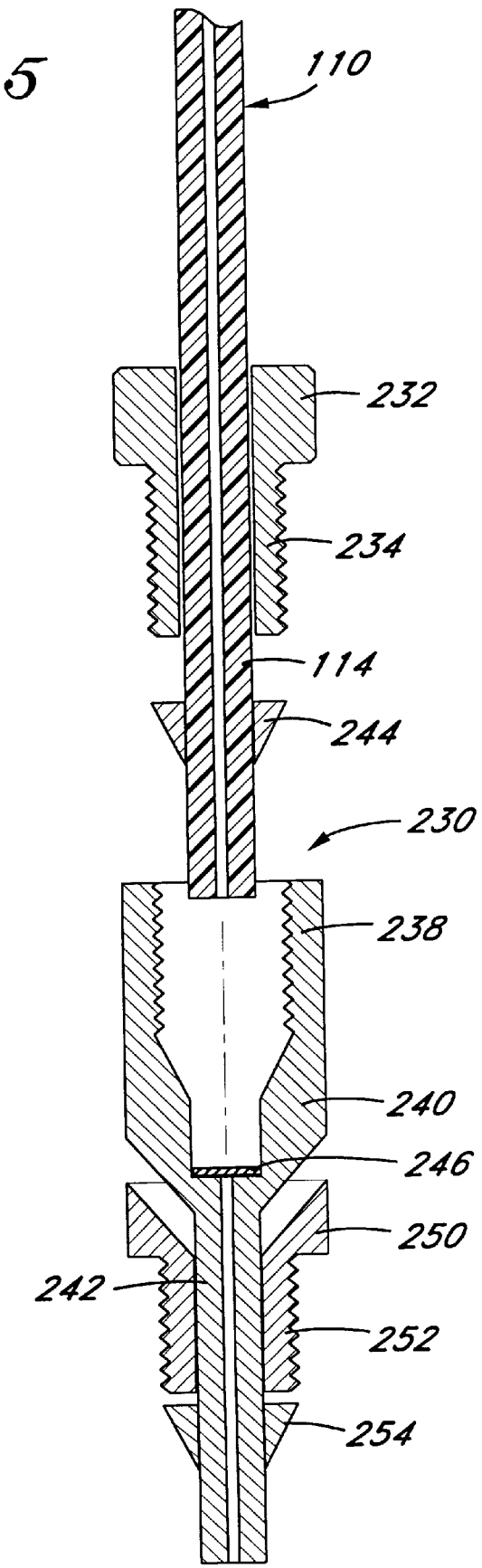
FIG. 5 is a cross-sectional view of a second embodiment of an end-fitting assembly for the capillary column of FIG. 3.

If it is desired to provide male instead of female connecting ports in the assembled column 110, a second embodiment of the end-fitting assembly 230 is illustrated in FIG. 5. The assembly 230 can replace the assemblies 120 and/or 206 and comprises a swaging nut 232 with a male screw portion 234 that engages a female screw portion 238 of an end nut 240. A conical ferrule 244 disposed between the swaging nut 232 and end nut 240 serves to radially grip and seal the shielded tubing 114 as the nuts 232 and 240 are tightened. A frit 246 is disposed at the end of the column 110. The end nut 240 has an elongated tubular portion 242 with a hollow, cylindrical aperture along its longitudinal axis.

A male connecting port is provided by a second swaging nut 250 with a male screw portion 252 coupled with a second ferrule 254 and the elongated portion 242 of the end nut 240. Therefore, a component with a female end portion can cooperate with the male connecting port in the same manner described above.

In FIG. 4b, the end nuts 132, 208 and swaging nuts 134, 198 are desirably made of stainless steel for strength, and more desirably coated in gold, which is softer and allows the components to seal more effectively. The same is true of the end nut 238 and swaging nuts 232, 250 in the second embodiment in FIG. 5. Advantageously, the more expensive graphite ferrules are not used in the present invention. Instead, the ferrules 136, 200, 244, 254 are economically made of stainless steel. These steel ferrules advantageously allow increased tightening pressure and provide a secure connection.

In the shielded column 110, the capillary 112 advantageously has a polyimide coating because an uncoated capillary 112' can easily break as it is slip-fitted into the shield tubing 114. A commercially available capillary 112 is coated with a polyimide layer that covers the external surface of the capillary 112 and has a thickness of about 1 $\mu$m. It is, however, feasible to use an uncoated capillary 112' if the shield tubing 114 is molded onto the uncoated capillary 112', or if the tubing 114 and uncoated capillary 112' are extruded at the same time. There is substantially less handling of the capillary 112' involved in molding or simultaneous extrusion than in producing a slip fit.

Furthermore, instead of providing a slip fit between the shield tubing 114 and the capillary 112, the tubing 114 and capillary 112 can be bonded together to form a single structure. A bonded capillary column 110" eliminates slip between the tubing 114 and capillary 112. The single structure formed by bonding the tubing 114 to the capillary 112 can prevent channeling between the capillary 112 and tubing 114.

Bonding can be achieved by injecting a bonding agent such as divinylbenzene (DVB) into the space between the capillary 112 and tubing 114 and allowing the DVB to polymerize. Because DVB shrinks, pressure may need to be applied to ensure a continuous bond along the length of the capillary 112. A variety of other bonding agents such as epoxy can be used. Advantageously, the epoxy used is sufficiently fluid and has a sufficiently low viscosity to be drawn into the space between the capillary 112 and tubing 114, and does not undergo substantial shrinking as it polymerizes, thereby eliminating the concern of a discontinuous bond and need for pressurization.

Preferred Dimensions and Performance Characteristics

To maintain low sample volume requirements and to increase performance efficiency, the capillary 112 desirably has an ID equal to or less than 700 microns ($\mu$m), i.e., 0.7 mm. The ID of the shield tubing or shielding 114 is slightly larger than the OD of the capillary 112, preferably with tight spacing that just permits a slip fit.

A fused silica capillary 112 can withstand an internal pressure of at least 9500 psi. This is significant because, although the column 110 is typically operated at about 500–1500 psi, it is packed anywhere between 2000 and over 9000 psi. The assembly thus provides high pressure capability with improved capability to withstand damage and handling during media packing.

The shield tubing or shielding 114 should be flexible so that the assembled capillary LC column 110 will also be flexible and can be assembled between the injector and the detector of an LC system directly, or with the help of a minimal length of connecting tubing, to reduce or eliminate extra column dead volume. The shielding 114 thus desirably is made of a flexible polymer. For high pressure applications, the shielding 114 must not be so soft and deformable that it cannot be assembled in packing processes that subject the shield 114 to high pressures. Because the first end 116 of the column 110 press against the frit 130 (FIG. 4a), the first end 116 of shield 114 is subjected to the same pressure used to pack the capillary column 112 with media. If the conical ferrule 136 does not adequately seal and grip the shield 114 and column 112, then either the shield 114 can be blown out of the ferrule 136, or fluid can be forced between the capillary 112 and shield 114 to inflate the shield 114. The same applies to ferrule 200 at the second end 118 as shown in FIG. 4b in pressurizing the column 112 for LC applications. The shield 114 allows the ferrules (e.g., 172, 200) to be tightened while reducing the risk of damaging fragile columns 112.

A commercially available polymer, "Victrex" PEEK, has found to perform well for high pressure liquid chromatography (HPLC). Therefore, the shielding 114 is preferably made of PEEK or other material with similar properties. Commercially available PEEK tubings for use as shielding 114 are flexible and can be cut to any desired length. They have $\frac{1}{16}$" to $\frac{1}{8}$" OD, and the ID is color-coded for easy identification. A $\frac{1}{16}$" PEEK tube is more flexible than a $\frac{1}{8}$" tube. PEEK tubings can be extruded to exacting tolerances with precise concentricity with a maximum error of ±0.001". For LC applications, the shielding 114 desirably has an ID that is just slightly greater than the OD of the capillary 112 for a slip fit.

PEEK is a semi-crystalline polymer which can take relatively high temperatures, as it has a melting point of 350° C., and can operate steadily at 100° C. The tensile properties of PEEK exceed those of most engineering plastics. At room temperature, a "Victrex" PEEK has a tensile strength that can range from about 100 MPa (at yield) to over 200 MPa (at break), depending on the grade. The tensile modulus falls between 9.6 and 13 GPa with a poison ratio of 0.4 to 0.45. The ultimate shear strength ranges from 53 to 97 MPa. The compressive strength (with flow) falls between 118 and 240 MPa.

PEEK has good creep properties for semi-crystalline polymers, even at high temperatures. Combined with good flexural and tensile characteristics, the creep properties of PEEK provide a good balance of properties for LC applications where the material is required to withstand high pressure loadings for long periods at high temperatures without a permanent deformation. For one grade of PEEK at room temperature under a load of 50 MPa, the strain increases from about 1.5% at 10 seconds to only about 1.9% at 10,000,000 seconds. The creep rupture time at 90 MPa is approximately 5,000,000 seconds.

The disclosed shielded capillary column has the following advantages over the prior art. It provides a simple device to protect the capillary from damage during manufacturing media packing, shipping, and handling. It provides an integrated assembling and packing process to save cost. It provides a more repeatable and exact column length. It provides a flexible LC column that can be connected easily and conveniently to an LC apparatus. Finally, it provides increased tightening pressure and secure connection with less chance of breaking, cracking or scratching the fragile fused silica columns during media packing and assembly.

It will be understood that the above described arrangements of apparatus and the methods therefrom are merely illustrative of applications of the principles of this invention and many other embodiments and modifications may be made without departing from the spirit and scope of the invention as defined in the claims.

What is claimed is:

1. A liquid chromatography column, comprising a silica based capillary column sized and dimensioned for chromatographic use, the column having a wall structure defining an internal cavity with first and second ends and a longitudinal axis, and a flexible, protective tubular shield that encloses the exterior of said wall structure for substantially the entire length of the capillary column, the shield being in addition to and encompassing any thin protective coating applied to the capillary column during manufacturing of the capillary column, the shield having a longitudinal axis that is substantially aligned with the longitudinal axis of the capillary column to provide a shielded capillary liquid chromatography column that is flexible and can be directly coupled to liquid chromatography equipment in order to minimize extra column dead volume.

2. The liquid chromatography column of claim 1, wherein the capillary column is made of fused silica.

3. The liquid chromatography column of claim 1, wherein the interior of the shield is slightly larger than the exterior of the capillary column to form a slip-fit between the shield and column.

4. The liquid chromatography column of claim 3, wherein the shield is a circular cylindrical tubing with an internal diameter slightly larger than the outer diameter of the capillary.

5. The liquid chromatography column of claim 4, wherein the shield is made of PEEK.

6. The liquid chromatography column of claim 1, wherein the shield is made of PEEK.

7. The liquid chromatography column of claim 6, wherein the capillary column is bonded to the shield using an epoxy.

8. The liquid chromatography column of claim 1, further comprising a first end-fitting at the first end of said liquid chromatography column and a second end-fitting at the second end of said liquid chromatography column, with said shield extending between and terminating inside said end fittings such that the length of the shield is substantially the same as the length of the capillary column.

9. The liquid chromatography column of claim 8, wherein the internal cavity of the capillary is filled with a packing material.

10. The liquid chromatography column of claim 9, wherein the first end-fitting has a first frit disposed at an opening at the first end of said liquid chromatography column and the second end-fitting has a second frit disposed at an opening at a second, opposing end of said liquid chromatography column, said first and second frits preventing the packing material from passing therethrough.

11. The liquid chromatography column of claim 10, wherein the first end-fitting further comprises:

a first end nut including a proximal end and a distal end, said proximal end having a first cavity with a first opening and said distal end having a second cavity with a second opening, and a passageway between said first cavity and second cavity, said first cavity having a seat occupied by the first frit and said first opening having a truncated conical cavity taper;

a first ferrule having a hollow center that is slip-fitted on said liquid chromatography column and a truncated conical taper to fit snugly onto said first opening of said proximal end; and a first swaging nut which cooperates with said proximal end to secure said first end nut with the first end of said liquid chromatography column.

12. The liquid chromatography column of claim 11, wherein the second end-fitting further has a second end nut including a proximal end and a distal end, said proximal end having a first cavity with a first opening and said distal end having a second cavity with a second opening, and a passageway between said first cavity and second cavity, said first cavity having a seat occupied by the first frit and said first opening having a truncated conical cavity taper;

a second ferrule having a hollow center that is slip-fitted on said liquid chromatography column and a truncated conical taper to fit snugly onto said first opening of said proximal end; and a second swaging nut which cooperates with said proximal end to secure said second end nut with the second end of said liquid chromatography column.

13. The liquid chromatography column of claim 11, wherein the second opening of the first end nut has a first female threaded portion and the second opening of the second end nut has a second female threaded portion.

14. The liquid chromatography column of claim 13, wherein said first and second end nuts, swaging nuts, and ferrules are made of stainless steel coated with gold.

15. A packed liquid chromatography column, comprising:

a silica based capillary column sized and dimensioned for chromatographic use, the column being filled with a packing material and having a thin coating on the exterior of the capillary column, and further enwrapped by a flexible, non-metallic shielding, the capillary column having a first open end and a second open end, the shielding being substantially coaxial with, and enwrapping the coated capillary column for substantially the full length of the capillary column, the capillary column being substantially filled with a packing media;

a first cover enclosing said first open end wherein said cover is liquid permeable but will not pass the packing media; and a second cover enclosing said second open end wherein said cover is liquid permeable but will not pass the packing media to provide a shielded capillary liquid chromatography column that is flexible and can be directly coupled to liquid chromatography equipment in order to minimize extra column dead volume.

16. The packed liquid chromatography column of claim 15, wherein the capillary is made of fused silica.

17. The packed liquid chromatography column of claim 15, wherein the flexible shielding is a PEEK tubing which is slip-fit onto the external surface of the capillary.

18. The packed liquid chromatography column of claim 15, wherein the first cover and second cover are circular discs having a diameter equal to or greater than the outer diameter of said liquid chromatography column.

19. The packed liquid chromatography column of claim 15, wherein the first cover and second cover are made of stainless steel.

20. A capillary liquid chromatography column formed by the steps of:
   providing a slurry which includes a packing material and a packing solvent;
   providing a silica based capillary column having a first open and a second open end, the column being sized and dimensioned for chromatographic use;
   slip-fitting a flexible, non-metallic shielding onto said capillary column so that a first end of said shielding is substantially flush with the first end of the capillary column and a second end of the shielding is spaced apart from the second open end of the capillary column, the shielding being in addition to and encompassing any thin protective coating applied to the capillary column during manufacturing of the capillary column;
   covering said first open end of the capillary column and at least a portion of the first end of the shielding with a first frit that allows said packing solvent but not said packing material to pass therethrough;
   injecting said slurry into said capillary column through said second open end while holding the capillary column by squeezing the shielding at the first and second ends of the shielding;
   cutting the second end of said capillary column flush with the second end of the shielding; and
   covering said second end of the capillary column with a second frit that allows a predetermined liquid, but not said packing material, to pass therethrough to provide a shielded capillary liquid chromatography column that is flexible and can be directly coupled to liquid chromatography equipment in order to minimize extra column dead volume.

21. The capillary of claim 20, wherein the capillary is fused silica.

22. A liquid chromatography column comprising:
   a silica based capillary tube sized and dimensioned for chromatographic use, the tube being coated at the time of manufacture with a thin protective layer and having a first open end and a second open end;
   a non-metallic, flexible tube enwrapping the capillary tubing for substantially the entire length of the capillary tube, and having an interior slightly larger than the exterior of the capillary tube to form a slip-fit between the flexible tube and the capillary tube, the flexible tube being substantially coaxial with the capillary tube;
   a first end-fitting connected to a first end of the flexible tube and forming a seal between the first end-fitting, the first end of the flexible tube and the first end of the capillary tube;
   a second end-fitting connected to a second end of the flexible tube forming a seal between the second end-fitting, the second end of the flexible tube, and the second end of the capillary tube to provide a shielded capillary liquid chromatography column that is flexible and can be directly coupled to liquid chromatography equipment in order to minimize extra column dead volume.

23. The column of claim 22, wherein the silica based capillary tube is made of fused silica.

24. The column of claim 23, wherein the flexible tube is made of PEEK.

25. The hardware of claim 22, further comprising packing material within the capillary tube.

26. The column of claim 22, wherein the ends of the capillary tube are substantially flush with the corresponding ends of the flexible tube.

27. The column of claim 22, wherein the ends of the capillary tube are substantially flush with the corresponding ends of the flexible tube.

28. The column of claim 22, wherein the capillary tube extends beyond one end of the flexible tube but not beyond the end fitting.

* * * * *